United States Patent [19]
Glück et al.

[11] Patent Number: 5,549,896
[45] Date of Patent: Aug. 27, 1996

[54] HEPATITIS A VIRUS STRAIN, METHOD FOR THE ISOLATION OF NEW HEPATITIS A VIRUS STRAINS AND HEPATITIS A VACCINES

[75] Inventors: Reinhard Glück, Spiegel/Bern; Stefan Brantschen, Bern, both of Switzerland

[73] Assignee: Schweiz. Serum- & Impfinstitut Bern, Bern, Switzerland

[21] Appl. No.: 386,207

[22] Filed: Feb. 9, 1995

Related U.S. Application Data

[63] Continuation of Ser. No. 960,410, Mar. 3, 1993, abandoned.

[30] Foreign Application Priority Data

May 8, 1991 [EP] European Pat. Off. .............. 91107526

[51] Int. Cl.⁶ .................. A61K 39/29; A61K 39/125; C12N 7/00; C12Q 1/70
[52] U.S. Cl. .................... 424/226.1; 435/235.1; 435/236; 435/237; 435/238; 435/5
[58] Field of Search .................. 435/235.1, 236, 435/237, 238, 5; 424/226.1

[56] References Cited

U.S. PATENT DOCUMENTS

| | | | |
|---|---|---|---|
| 4,559,229 | 12/1985 | Page et al. | 424/89 |
| 4,614,793 | 9/1986 | Hughes et al. | 530/350 |
| 4,870,026 | 9/1989 | Wands et al. | 424/89 |
| 5,021,348 | 6/1991 | Giesa et al. | 435/237 |

FOREIGN PATENT DOCUMENTS

| | | | |
|---|---|---|---|
| 0008559 | 3/1980 | European Pat. Off. | C12N 7/08 |
| 0025745 | 3/1981 | European Pat. Off. | C12N 7/08 |
| 2398504 | 2/1979 | France | A61K 39/12 |

OTHER PUBLICATIONS

Gust, I. D. 1990 *British Medical Bulletin* vol. 46 pp. 319–328.
Mao, J. S. et al. 1989. *J. Infectious Diseases* vol. 159 pp. 621–624.
Locarnini, S. A. et al. 1978. *Intervirology* vol. 10 pp. 300–308.
Scholtz, E. et al. 1989. *J. Gen. Virol.* vol. 70 pp. 2481–2485.
Sjogren, M. H. et al. 1992, *Vaccine* vol. 10 Suppl. 1 pp. 5135–5137.
Tilzey, A. J. et al. 1992, *Vaccine* vol. 10 Suppl. 1 pp. 5121–5123.
Just, M. et al. 1992, *Vaccine* vol. 10 Suppl. 1 pp. 5110–5113.
Andre, F. E. et al. 1992, *Vaccine* vol. 10 Suppl. 1 pp. 5160–5168.
Goubau, P. et al. 1992, *Vaccine* vol. 10 Suppl. 1 pp. 5114–5118.
Lemon, S. M. et al. 1992, *Vaccine* vol. 10 Suppl. 1 pp. 540–544.

*Primary Examiner*—Mary E. Mosher
*Attorney, Agent, or Firm*—Fish & Richardson P.C.

[57] ABSTRACT

The invention relates to hepatitis A viruses (HAVs) having a serotype displaying the immunological characteristics of the HAV strain RG-SB XA112 (CNCM I-1080). In particular, the invention relates to the new hepatitis A virus strain RG-SB XA112 (CNCM I-1080). The invention also relates to structural components of said HAVs. Furthermore, the invention relates to processes for the isolation of said HAVs. The HAVs of the present invention and the structural components thereof can be used for the production of vaccines and diagnostic compositions. Finally, the invention relates to polyclonal and monoclonal antibodies which are directed to said new HAVs.

6 Claims, No Drawings

HEPATITIS A VIRUS STRAIN, METHOD FOR THE ISOLATION OF NEW HEPATITIS A VIRUS STRAINS AND HEPATITIS A VACCINES

This is a continuation of application Ser. No. 07/960,410 filed on Mar. 3, 1993, now abandoned.

The invention relates to hepatitis A viruses (HAVs) having a serotype displaying the immunological characteristics of the HAV strain RG-SB XA112 (CNCM I-1080). In particular, the invention relates to the new hepatitis A virus strain RG-SB XA112 (CNCM I-1080). The invention also relates to structural components of said HAVs. Furthermore, the invention relates to processes for the isolation of said HAVs. The HAVs of the present invention and the structural components thereof can be used for the production of vaccines and diagnostic compositions. Finally, the invention relates to polyclonal and monoclonal antibodies which are directed to said new HAVs.

Hepatitis A infection is endemic in most less developed areas of the world, with widespread contamination of food and water supplies presenting a special risk to travellers from more developed areas. In developed countries, outbreaks associated with day care centers, handling diapered children and with drug abuse and homosexual activity are being increasingly recognized. Hepatitis A virus (HAV), classified as an enterovirus within the picornavirus family, is difficult to isolate in cell culture, grows poorly in early in vitro passages and generally is not cytopathogenic. The genome of the virus has been cloned and sequenced and only one serotype has been identified. Although infection with HAV never becomes chronic, it is the cause of significant human morbidity and loss of productivity.

For these reasons, there will be a future need for prophylaxis against hepatitis A virus. Passive immune prophylaxis is effective but of only temporary benefit and active immunization would be a more practical approach to the control of the infection.

Considerable progress has been made in the development of hepatitis A vaccines. Conventional inactivated and live-attenuated vaccines have been prepared from HAV replicated in cell culture. Recombinant DNA technology has been applied to develop alternative approaches to the development of hepatitis A vaccines. These approaches include expression of viral antigens in vitro, the use of live virus vectors for expression of viral antigens in vivo and the production of synthetic peptides representing gene products of the virus (Bulletin of the WHO, 66 (4) (1988), 443).

Since the important epitope for neutralization of the virus appears to be conformational rather than linear, further research will be necessary before hepatitis A vaccines based upon these new technologies become available. The feasibility of developing a conventional formaldehyde-inactivated HAV vaccine was demonstrated before the era of successful growth of HAV strain CR 326 in vitro, which was partially purified from the liver of acutely infected S. Labiatus marmosets (Provist, P. J. and Hilleman, M. R., Proc. Soc. Exp. Biol. Med.; 159 (1978), 201). Multiple aqueous doses of vaccine were administered to S. Labiatus marmosets. All animals immunized in this manner developed antibodies, and all were immune to challenge infection. Subsequently, a highly purified, formaldehyde-inactivated HAV vaccine was prepared from the same strain grown in LLC-MK2 cell culture, a transformed Rhesus monkey kidney cell line. This vaccine, however, is currently not acceptable for human vaccine development (Provist, P. J. et al. J. Med. Virol., 19 (1986), 23). Other prototype formaldehyde-inactivated HAV vaccines were prepared in other transformed cell lines or by passing through primary animal cell cultures: Merck & Co., Inc., (Provost, P. J., Hilleman, M. R. and Hughes, J.), U.S. patent Ser. No. 79-71648, U.S. patent Ser. No. 80-171621 and U.S. patent Ser. No. 83-541836, U.S. Dept. of Health and Human Services (Robertson), U.S. patent Ser. No. 88-211973, Seelig, R. et al., EP 84-105066, Behringwerke AG (Lorenz), EP 7461, U.S.A. (Daemer et al.) U.S. patent Ser. No. 84-652067A.

Vaccines produced in such a manner have the following drawbacks:

(1) foreign antigens and genetic material from the growth substrate capable of inducing an allergic or oncogenic reaction may be contained in the vaccine;

(2) unknown agents originating from the passages through animal cell cultures may be contained in the vaccine;

(3) antibiotics contained in the vaccine may induce allergic reactions in sensitized individuals;

(4) the safety and immunogenicity of such HAV vaccines have not been sufficiently demonstrated in humans. An important advance in inactivated hepatitis A vaccine development has been the propagation of HAV in human fibroblast cultures without previous passaging in animals (Flehmig, B., EP 82-108268). The HAV was isolated from the stool of a patient with acute hepatitis A infection and propagated in primary human kidney cells. Further passages in human diploid fibroblast cells yielded the HAV antigen for the production of an inactivated hepatitis A vaccine. The vaccine produced in such a manner still has the following drawbacks:

(I) isolation of HAV from stools and further cultivation on primary human cells without chemical pretreatment of the isolate still contains a potential risk of contamination with unknown extraneous agents, (II) serial passaging of HAV in human fibroblast cell culture yields large quantities of defective interfering particles (DI) (Calein and Roux, L., J. Virology, 62/8 (1988), 2859), which reduce the immunological potential of such vaccines, (III) the above mentioned DI suppress high titer harvests of HAV: therefore a vaccine produced in such a manner would be extremely expensive, (IV) the described HAV antigen is inactivated with a formaldehyde solution at a final dilution of 1:2000 in $H_2O$ and stirred for 12 days at 37° C. This procedure denatures the HAV antigen so that the protective potential of the vaccine may be lost, and (V) the antigen developed in this manner didn't show a protective antibody titer against all hepatitis A isolates tested from all continents of the world.

Thus, the technical problem underlying the present invention is to provide an optimally tolerated hepatitis A vaccine capable of eliciting a high antibody titer and having superior immunological properties.

The solution to this technical problem is achieved by providing the embodiments characterized in the claims. In particular, it is achieved by providing HAVs having a serotype displaying the immunological characteristics of the HAV strain RG-SB XA112 (CNCM I-1080) which was deposited under the requirements of the Budapest Treaty at the Collection Nationale de Cultures de Microorganismes (CNCM) of the Institut Pasteur, Paris, on Apr. 11, 1991, under the deposition number I-1080.

In a preferred embodiment the invention relates to the new HAV strain RG-SB XA112 (CNCM I-1080).

The above HAV displays superior immunogenic properties and furthermore induces a broad scope of protection against HAV infections. This is because the immune response induced by the new HAV strain is mediated by antibodies which also recognize most of the presently known other HAV serosubtypes.

The HAV of the present invention and the corresponding vaccines differ from the prior art in that 1st: The virus isolated from the stool of a patient with an acute hepatitis A infection has been purified by different physical purification methods and treated with an acid solution of pH 1 to remove all possible extraneous agents originating from the patient;

2nd: The virus has directly been passaged on human diploid cells of a controlled cell bank (a controlled cell bank is a bank wherein the cells have been extensively tested for the absence of extraneous contaminations or abnormalities) for vaccine production without passaging on primary animal or human cells, which reduces further contamination by these cells. In this context, the term "primary animal or human cells" refers to cells which are freshly isolated from animals or humans. They are not uniform in their nature and passaging of these cells is not possible. Therefore, an extensive testing procedure for the detection of abnormalities or contaminations cannot be carried out with these cells;

3rd: The passaging of the virus on human diploid cells has been performed in such a manner that the occurrence of DI has been avoided; and 4th: The viral antigen has been carefully treated by chemical agents to avoid denaturation of the proteins.

The present invention furthermore relates to the structural components of the HAV of the present invention. Preferably, these structural components are the viral mRNA, the core protein, or the VP (Viral Protein) 1, VP2, VP3 or VP4 protein. The invention furthermore relates to biologically active or functional parts or derivatives of said structural components. A biologically active part of such structural components is for instance a part of VP1 which still induces the formation of anti-HAV antibodies and neutralizes active virus.

In a particularly preferred embodiment, the structural components of the HAV of the present invention are involved in causing the immunological characteristics of the HAV strain RG-SB XA112 (CNCM I-1080) of the present invention.

This deposit was made under the provisions of the Budapest Treaty on the International Recognition of the Deposit of Microorganisms for the Purpose of Patent Procedure and the Regulations thereunder (Budapest Treaty) on Apr. 11, 1991. This assures maintenance of a viable culture for 30 years from the date of deposit. The organism will be made available at Collection Nationale de Cultures de Microorganismes (CNCM) under the terms of the Budapest Treaty, which assures permanent and unrestricted availability of the progeny of the culture to the public of any U.S. or foreign parent application, whichever comes first and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638).

In another embodiment, the present invention relates to a process for the isolation of HAV viruses comprising the following steps:

(a) Suspending stool of an acute phase HAV infected patient in a buffer solution;

(b) centrifugation of the suspension;

(c) ultracentrifugation of the supernatant;

(d) isolation of the virus containing fraction and dialysis thereof;

(e) infection of human diploid cells from a controlled cell bank with the virus preparation of (d);

(f) cultivation of the infected cells;

(g) passaging the cells of step (f) and assaying the passages for HAV activity;

(h) isolation of a virus containing cell extract of HAV positive passages of step (g); and (i) further passaging and subsequent cloning of HAV strains by endpoint dilution, preferably after each third passage, wherein said virus containing suspension or fraction is treated with an acid having a pH of lower than 2, preferably of 1, before infecting said human diploid cells.

It is known that only the enteroviruses show stable infectivity at pH 1. All other viruses are inactivated at this low pH. In comparison to other enteroviruses, HAV exhibits an extremely high stability at this low pH. We could show that from all human enteroviruses only HAV was still infectious after 5 hours of incubation at 37° C. and pH 1. The employed procedure permits the conclusion that a contamination of the isolate with another human extraneous infectious agent can be excluded.

In a preferred embodiment of the process of the present invention, the cultivation and passaging up to step (g) is carried out at 37° C. and the further passaging and cloning of step (i) is carried out at 32° C.

The "cold adaptation process" to 32° C. in human diploid cells leads to an attenuated HAV which is much less pathogenic in humans than a virus adapted at 37° C.

The term "attenuated HAV" in this context refers to an HAV whose pathogenicity is reduced.

In another preferred embodiment of the process of the present invention, the host cells for the virus multiplication are human diploid finite life cells, preferably MRC-5 (available from the American Type Culture Collection (ATCC) under deposition number ATCC CCL 171), MRC-9 (ATCC CCL 212) or WISTAR 38 cells. The term "human diploid finite life cells" refers to cells which undergo about 60 cell cycles in culture before they die. The advantage of the use of these cells lies in their safety as substrates. The finite life cells used underly extensive control concerning the absence of adventitious microbial agents including retroviruses, chromosomal abnormalities or oncogenic potential. In addition, it is evident that cells with a uniform population doubling (PD) level and prepared from a cell bank (depositary) give more reproducible results than primary cells from different individuals.

In another embodiment, the present invention relates to an HAV vaccine containing a non-pathogenic, immunogenic derivative of an HAV of the present invention, the HAV strain RG-SB XA112 (CNCM I-1080) of the present invention, and/or an immunogenic structural component of any of the HAVs of the present invention, and optionally a pharmaceutically acceptable carrier, adjuvant and/or diluent.

Besides the use of intact whole, inactivated HAV, a single or a combination of the four subunit capsid proteins VP1, VP2, VP3 and VP4 can be used for vaccine preparation. The whole virus or the subunit components can be adsorbed to known carrier materials such as aluminum hydroxide, aluminum phosphate, other viruses, liposomes, virosomes or immunosomes to enhance immunogenicity.

In a preferred embodiment of the HAV vaccine of the present invention, said derivative of said HAV is a chemically attenuated HAV or a non-pathogenic HAV strain which is additionally chemically attenuated.

A vaccine containing a chemically attenuated HAV refers to a vaccine which contains a precisely determined quantity of active virus in addition to the inactivated virus. It is thus a mixture of attenuated and inactivated types of vaccine as it has been described for rabies vaccine type "Fermi" (L épine, P.: Laboratory Techniques in Rabies (WHO), 3rd edition, 1973, 199). Such a vaccine can be produced by limiting the formaldehyde concentration (e.g. 1:4000) and limiting the inactivation time and temperature (e.g. 4 days at 4° C.). The advantage of such a vaccine lies in the higher immunogenicity: The inactivated particles stimulate the human immune system immediately after administration to human beings whereas the attenuated, cold adapted live HAV needs some time to replicate in the body before eliciting an immune response. Since the immune cells are only stimulated by the large amount of inactivated virus, but not by the small live virus fraction until it replicates, the live virus fraction infects its target cells, undergoes replication and after replication acts as an effective booster dose.

In another preferred embodiment of the HAV vaccine of the present invention, at least one of the HAV strains contained therein is HAV strain RG-SB XA112 (CNCM I-1080).

In a preferred embodiment of the present invention, the viruses contained in said vaccines have been chemically attenuated by formaldehyde or β-propiolactone (BPL) treatment. This principle of chemical attenuation can also be employed for the preparation of other viral vaccines such as containing the influenza virus, respiratory syncytial virus, or rotavirus.

Formaldehyde is known to chemically influence the capsid proteins in such a way that the virus is no longer able to be infectious without losing its immunogenicity. Instead of formaldehyde, β-propiolactone (BPL) can also be used as an inactivating agent.

In a preferred embodiment, the present invention relates to polyclonal or monoclonal antibodies which are specifically directed to the the HAVs of the present invention or to a structural component thereof. These antibodies of the present invention do not display any cross-reactivity with any other HAV serosubtypes known from the prior art. Thus, the provision of the new HAVs of the present invention for the first time allows the production of such specific polyclonal or monoclonal antibodies.

In another preferred embodiment, the antibodies are directed to the HAVs of the present invention or to a structural component thereof and display a cross-reactivity with most other HAV serosubtypes known from the prior art. Thus, the provision of the new HAVs of the present invention for the first time allows the production of polyclonal or monoclonal antibodies with a broad spectrum so as to recognize most of the human HAV serosubtypes.

The polyclonal antibodies can be prepared by immunizing spf (specific pathogen-free) animals (e.g. sheep) with an HAV of the invention, e.g. strain RG-SB XA112 (CNCM I-1080), inactivated, partially inactivated or live or a structural component thereof and by purifying the collected serum by known techniques. The monoclonal antibodies can be produced by immunizing human volunteers with a hepatitis A vaccine containing an inactivated, chemically attenuated or live HAV of the invention, e.g. strain RG-SB XA112 (CNCM I-1080), or a structural component thereof. Two weeks after successful immunization the stimulated lymphocytes can be isolated from the blood and fused with cells of a human myeloma cell line. The hybridomas thus obtained which synthesize the desired monoclonal antibody, can be selected by testing the cell culture medium containing the fused cells for the presence of said desired monoclonal antibody.

Finally, the present invention relates to a diagnostic composition containing the HAVs of the present invention or a non-pathogenic derivative thereof, HAV strain RG-SB XA112 (CNCM I-1080) or a non-pathogenic derivative thereof, a structural component of any of the HAVs of the present invention, or an antibody as set forth above.

The HAV antigen can e.g. be used to coat ELISA plates to detect HAV antibodies in the serum of a patient. The antibodies can e.g. be used to prepare conjugates for radio-immuno assays.

EXAMPLE 1

Isolation of HAV strain RG-SB from infectious material

Wild type HAV was obtained from stool of a patient in the acute phase of hepatitis A infection by suspension of the stool in a phosphate buffer solution, pH 7.4, centrifugation, pelleting the virus in the supernatant by ultracentrifugation through a sucrose cushion of 30% saccharose and further purified by density gradient ultracentrifugation using a $CsCl_2$ gradient with a density between 1.1 and 1.5 g/ml. HAV containing fractions were identified by a modified solid phase RIA technique. This modification refers to the determination of antigen instead of antibody. Said determination can be achieved by carrying out a so-called competition test: A constant quantity of anti-HAV antibodies is mixed with the HAV antigen. The amount of unbound antibodies which is then determined is a measure of the quantity of HAV antigen that neutralized the bound anti-HAV antibody portion.

The fraction with a density of about 1.3 g/ml was dialyzed twice against a physiological saline solution. The pH of the solution was adjusted with HCl (1 m) to pH 1. After 5 hours at room temperature the pH was adjusted with NaOH (10%) to pH 7.

EXAMPLE 2

Adaptation of HAV to human diploid cells (MRC-5)

Purified wild-type virus was adapted to MRC-5 (ATCC CCL 171) cells by mixing 1 ml of the isolated HAV material from Example 1 with 10 ml of a suspension containing BME medium (Gibco) and $10^7$ MRC-5 cells. The process of adaption enables the virus to replicate in said MRC-5 cells. This suspension was kept at room temperature and gently stirred every 10 minutes. After one hour, the suspension was transferred to a Corning tissue flask with a surface of 150 $cm^2$ and 70 ml of BME with 10% FBS was added. This was followed by adding $CO_2$ to the gas phase in the tissue flask to a final concentration of 5% and incubation at 37° C. The HAV-infected MRC-5 cells were split every week at a ratio of 1:2. One half of these cells was used for the adaptation process, the other cells for the testing for HAV antigen. After 10 blind passages (i.e. passages without the detection of HAV), HAV antigen could be detected for the first time using the modified RIA. For this purpose, the cell-associated virus was extracted by freezing-thawing the content of the Corning flasks three times and by subsequent ultrasonication. Cell debris was removed by low speed centrifugation.

For further attentuation the HAV of the 13th blind passage was used. The virus was isolated after breaking up the cells by freezing-thawing.

EXAMPLE 3

Attenuation of HAV strain RG-SB on MRC-5 cells

Confluent MRC-5 cell cultures grown in 75 cm$^2$ plastic flasks (Corning) were washed twice with BME medium and inoculated with 1.0 ml of vital inoculum containing the adapted HAV. After a four-hour period of viral adsorption at 32° C., BME medium containing 10% FBS was added. The cultures were incubated at 32° C. and the medium was replaced thereafter at seven-day intervals. After each passage, the virus was extracted and passed onto a new freshly confluent tissue culture. The second passage lasted 4 weeks, the third one 3 weeks and the fourth one 2 weeks. After each passage, the virus was extracted from the lysate of the cells by freezing-thawing. After the fourth passage, several inocula were prepared for the fifth passage making endpoint dilutions of $10^{-5}$ to $10^{-9}$. The virus from the culture with the highest dilution in which virus could be detected was then used for further passaging. Passages were performed by incubating the virus-adsorbed cells at 32° C. for 2 weeks (the medium was changed after one week) and by employing an endpoint dilution passage after each two passages. This procedure was repeated until the 23rd passage which yielded the adapted and attenuated production seed virus (i.e. the virus from this passage was used for the production of the vaccine) for hepatitis A vaccine.

EXAMPLE 4

Production of a live attenuated hepatitis A vaccine

Large quantities of MRC-5 cell cultures were grown in NUNC cell factories (NUNC, Copenhagen, Denmark). Dense cell layers were infected with HAV strain RG-SB XA112 (CNCM I- 1080) from the production seed with a multiplicity of infection of about 0.1. The virus was adsorbed for 4 hours at 32° C. Fresh BME medium containing 10% FBS was then added to the infected cells and thereafter the cell factories were incubated at 32° C. After one week of incubation, the medium was replaced with fresh medium. After another week of incubation, the HAV was extracted from the cell culture. An extraction solution containing 100 mM borate and 5 mM Na-EDTA, adjusted to pH 8 with 10% NaOH, was added to the cultures. Subsequently, the NUNC cell factory was moved to a deep-freezing chamber at −30° C. After complete freezing of the cells, the cell factory was transferred to an incubation room of 37° C. until the suspension had thawed. This procedure was repeated twice. The suspension was then pumped into centrifugation bottles and treated with ultrasonication (Bransonic, Branson Europe BV, frequency 50 kHz ±10%). Ten seconds of ultrasonic shocks repeated twice, after intervals of 10 seconds each, yielded the best result.

The suspension was then centrifuged for 10 minutes at 2500 xg and the supernatant was transferred into a bottle. The pellet was resuspended with half the volume of the extraction solution and freeze-thawed again, followed by ultrasonication and centrifugation. This procedure was repeated once and all the supernatants were finally pooled. Then the supernatants were clarified by filtration and sterile filtered through a membrane filter of pore size 0.2 μm (Millipore).

These supernatants containing the active pharmaceutical ingredient were stored at −30° C. until the vaccine was blended.

The final bulk vaccine was prepared under sterile conditions and contained the following components:

| | |
|---|---|
| Attenuated HAV virus, strain RG-SB XA112 (CNCM I-1080) | $10^{7.3}$ TCID$_{50}$/ml |
| NaCl | 3.4 mg/ml |
| Polygeline or Physiogel (Hausamman) | 16.0 mg/ml |
| Phenolred (Sigma) | 20 μg/ml |
| Sucrose | 340 μg/ml |

EXAMPLE 5

Production of an inactivated hepatitis A vaccine

HAV virus, strain RG-SB XA112 (CNCM I-1080), was prepared according to Example 4. The filtered supernatants were further purified by:

Concentration by ultrafiltration (Minitan, Millipore);

purification by ultracentrifugation through a 30% sucrose cushion solution (24 hours, 100'000 xg);

resuspension of the pellet in 5 mM Na-EDTA, 100 mM borate, pH 8;

further purification by ultracentrifugation through a CsCl$_2$ gradient with a density between 1.1 and 1.5 g/ml at 100'000 xg;

pooling of fractions containing HAV (d<1.35–d>1.23);

transfer of the fractions into a dialysis tubing (Spectra, Por, Molecular cut off 12'000–14'000) and dialysis against 0.9% NaCl at 4° C., 3×12 hours;

inactivation of the HAV suspension with formaldehyde (1:2000 dilution in H$_2$O), 3.5 days at 37° C. and 6 days at room temperature;

elimination of formaldehyde by dialysis or ultracentrifugation (see above);

dilution of the inactivated HAV suspension with a 0.9% NaCl solution to an antigen concentration of 1000 ng/ml;

adsorption of the antigen to an adjuvant (e.g. Al(OH)$_3$ or liposomes) by mixing equal amounts of the HAV suspension and the adjuvant solution (in the case of Al(OH)$_3$ a stock solution of 0.8% was used).

Filling of 0.5 ml aliquots into vaccine vials.

EXAMPLE 6

Production of a partially inactivated hepatitis A vaccine (chemically attenuated)

The vaccine was prepared according to Example 5 with the following modification:

Instead of complete inactivation the purified HAV suspension was chemically attenuated by treatment with a formaldehyde solution (diluted 1:2000 in H$_2$O). The suspension was stirred at 4° C. for 4 days. Formalin was removed by pelleting the virus twice by ultracentrifugation (100'000 xg, 1 hour). The HAV was resuspended in a 0.9% NaCl solution and then diluted to an antigen concentration of 100 ng per vaccine dose.

EXAMPLE 7

Vaccination of human volunteers with vaccines containing the HAV strain RG-SB XA112 (CNCM I-1080)

Three hepatitis A vaccines were prepared according to Examples 4, 5 and 6. All vaccines met the standards of international control authorities for inactivated and live attenuated vaccines produced in human diploid cells.

15 healthy seronegative adults were immunized orally with $10^5$ tissue culture infectious dose 50% ($TCID_{50}$) of vaccine produced as described in Example 4 (Vaccine A). At a $TCID_{50}$, 50% of all cells in the culture are infected when the virus stock solution is diluted by a factor of $10^5$.

15 healthy seronegative adults were immunized parenterally with an inactivated hepatitis A vaccine containing 250 ng of inactivated HAV antigen as described in Example 5 (Vaccine B).

Another group of 15 healthy seronegative adults was immunized parenterally with a chemically attenuated hepatitis A vaccine containing 100 ng of inactivated HAV antigen and $10^5$ $TCID_{50}$ of HAV produced according to Example 6 (Vaccine C).

Vaccine A was administered once, vaccines B and C were administered according to the following schedule: Two vaccinations on day 0 and a booster dose on day 7. Antibody titers of all volunteers were monitored on day 28 for vaccine A and on day 21 for vaccines B and C. Anti-HAV antibodies were determined with a commercially available RIA-kit (Abbott). The results are shown in Table 1.

TABLE 1

| Vaccine Group | Antibody titer in serum Geometric mean value (mIU) | Seroconversion n = 15 % |
| --- | --- | --- |
| A | 769 | 100 |
| B | 359 | 100 |
| C | 1231 | 100 |

The results indicate that all HAV preparations containing strain RG-SB XA112 (CNCM I-1080) were highly immunogenic. All vaccines showed a significant seroconversion after vaccination.

In addition, all three vaccines were well tolerated: No systemic and only a few local reactions were reported after vaccination. In no group could enhanced liver enzyme values be detected.

EXAMPLE 8

Neutralization of different HAV strains with serum from volunteers vaccinated with the HAV strain RG-SB XA112 (CNCM I-1080)

Neutralization tests employing eight strains of HAV recovered from widely diverse geographic areas were carried out on serum specimens obtained from human volunteers after vaccination with the HAV strain RG-SB XA112 (CNCM I-1080). The serum from each volunteer neutralized HAV from Kansas (LV-374), Alaska (FrAL), Germany (Gr8), Panama (PA21), North Africa (MBB), Australia (HM-175), Switzerland (CLF) and Shanghai (Shanghai). These results indicate that the vaccine will protect against HAV from different parts of the world.

EXAMPLE 9

Production of polyclonal antibodies directed to HAV strain RG-SB XA112 (CNCM I-1080)

In order to obtain a potent polyclonal serum for use as a diagnostic tool for HAV antigen determination or anti-HAV antibody measurement, adult spf sheep were immunized with a vaccine prepared according to Example 5 on days 0, 7, 14 and 44. On day 0, four doses were administered i.m. to each sheep at different sites (thighs). On days 7, 14 and 44, two doses were injected i.m. into both hindlegs. On day 58, 350 ml of blood was collected from each sheep. The serum fraction was separated and further purified according to known techniques (Cohn, E. J. et al., J. Amer. Chem. Soc., 69 (1946), 459.).

EXAMPLE 10

Production of human monoclonal antibodies (HMAB) directed to HAV strain RG-SB XA112 (CNCM I-1080)

Adult volunteers received two intramuscular injections of the vaccine prepared according to Example 4 on day 0 and a booster dose on day 7 in the deltoid region. Human peripheral blood lymphocytes (PBL) were obtained from donors on day 28. Mononuclear cells were separated on a Ficoll-Hypaque density gradient (Pharmacia, Uppsala, Sweden) and monocytes were depleted by adherence to plastic. Non-adherent cells were then tested in antigen-specific panning assays as follows: The cells were centrifuged and resuspended in cold PBS (pH 7.4) containing 1% BSA. Lymphocytes ($10^7$/ml in PBS containing 1% BSA; PBS/BSA solution) were added to each well of a 6-well plate (Costar, Badhoevedorp, Netherlands), previously coated with HAV antigen. To block the remaining unspecific binding sites on the plastic surface, the wells had been incubated with the PBS/BSA solution for at least 1 hour at 4° C. After incubation for 70 minutes, the non-adherent cells were aspirated. IMDM cell culture medium (Sigma Chemical Co., St. Louis, Mo.) containing 10% fetal calf serum (FCS) and an equal volume of Epstein-Barr virus (EBV containing supernatant from a culture of the B 95-8 marmoset cell line) were added to the adherent cells. The cells were cultured at 37° C. for 3 hours. After incubation, the cells were washed and distributed into 96 well microtiter plates containing IMDM plus 10% FCS, 30% conditioned medium from the lymphoblastoid cell line JW5, $5 \times 10^{-5}$M 2-mercaptoethanol, 50 µg/ml gentamycin sulfate (Sigma), and 600 ng/ml cyclosporine A (Sandimmun, Sandoz, Basel, Switzerland) at a density of $10^4$ to $10^5$ cells/well. After 14 to 21 days of incubation, culture supernatants were screened by ELISA for antibody binding to HAV, strain RG-SB XA112 (CNCM I-1080). Cell cultures form positive wells were expanded, retested by ELISA, subcultured at low density and further tested by immunoblotting and immunofluoroescence. After further expansion, the cells were fused with the 6-thioguanine/ouabain resistant F3B6 (NS1×human B cell hybrid) heteromyeloma cell line by the plate fusion technique (Larrick, J. W., Human Hybridomas and Monoclonal Antibodies, Plenum Press, New York, 1985, p. 446). Hybrids were selected in IMDM containing 100 µM hypocanthine, 5 µg/ml azaserine and 5 µM ouabain and cultured in microtiter plates without a feeder layer. Hybridomas with supernatants containing antibodies which specifically bound HAV RG-SB XA112 (CNCM I-1080) (neutralization tests) were cloned by limiting dilution and HMAb secreted by the cells were harvested.

We claim:

1. A biologically pure hepatitis A virus (HAV) culture RG-SB XA112 (CNCM #I-1080).

2. The HAV according to claim 1 wherein the virus has been inactivated.

3. An HAV vaccine comprising the HAV according to claim 1 or 2.

4. The HAV vaccine of claim 3 which further comprises a compound selected from the group consisting of a pharmaceutically acceptable carrier, an adjuvant and a diluent.

5. A method for the prophylaxis of HAV infections comprising administering the vaccine of claim 3 to a patient in need thereof.

6. A diagnostic composition comprising the HAV of claim 1 or 2.

* * * * *